United States Patent [19]

Knifton

[11] 4,172,087
[45] Oct. 23, 1979

[54] PROCESS FOR PREPARING UNSATURATED ALIPHATIC ESTERS FROM ALIPHATIC DIENES

[75] Inventor: John F. Knifton, Austin, Tex.

[73] Assignee: Texaco Development Corporation, White Plains, N.Y.

[21] Appl. No.: 877,439

[22] Filed: Feb. 13, 1978

[51] Int. Cl.² .......................... C09F 5/08; C11C 3/00; C11C 1/00; C07C 67/36
[52] U.S. Cl. ............................ 260/410.6; 260/408; 260/410; 260/410.5; 260/410.9 R; 260/413; 260/410.7; 560/207; 562/497; 562/522; 562/406
[58] Field of Search ...................... 260/408, 410, 410.5, 260/410.6, 410.9 R, 410.9 C, 413 R, 413 HC; 560/207; 562/497, 522

[56] References Cited

U.S. PATENT DOCUMENTS

| | | | |
|---|---|---|---|
| 3,437,676 | 4/1969 | Kutepow et al. | 562/522 |
| 3,455,989 | 7/1969 | Kutepow et al. | 260/410.9 C |
| 3,530,155 | 9/1970 | Fenton | 260/410.9 C |
| 3,780,074 | 12/1973 | Romanelli | 260/410.9 C |

*Primary Examiner*—John Niebling
*Attorney, Agent, or Firm*—Thomas H. Whaley; Carl G. Ries; Bernard Marlowe

[57] ABSTRACT

This invention relates to the selective production of fatty acid derivatives from aliphatic diene substrates, such as 1,3-butadiene, in the presence of dual-function homogeneous palladium complexes and certain classes of organic tertiary nitrogen bases.

11 Claims, No Drawings

PROCESS FOR PREPARING UNSATURATED ALIPHATIC ESTERS FROM ALIPHATIC DIENES

SUMMARY OF INVENTION

This invention concerns a process for preparing unsaturated aliphatic carboxylic acids and their ester derivatives from aliphatic conjugated dienes.

More specifically, this inventive process relates to the selective co-synthesis of two classes of linear unsaturated carboxylic (fatty) acids and their ester derivatives via the one-step carbonylation and concurrent dimerization, carbonylation of conjugated aliphatic dienes, such as 1,3-butadiene, in the presence of hydroxylated co-reactants, homogeneous dual-function palladium catalysts and certain classes of organic, nitrogen-containing, tertiary bases. The process is exemplified by, but not limited to, the one-step carbonylation and dimerization, carbonylation of 1,3-butadiene to 3-pentenoic acid, 3,8-nonadienoic acid and their corresponding ester derivatives, according to the stoichiometry of eq. 1 and 2.

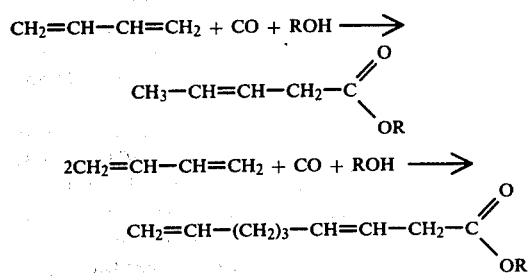

The inventive process, more fully described infra, has the advantages over the prior art* of ensuring improved palladium catalyst stability during the one-step dimerization and carbonylation of said conjugated diene substrates, improved selectivity to two classes of linear, unsaturated carboxylic acid/ester derivatives and improved palladium catalyst performance upon recycle with fresh diene substrate.

* See: J. Tsuji et al, Tetrahedron 28, 3721 (1972), W. E. Billups et al, J.C.S. Chem. Comm. 1067 (1971).

The products, particularly the esters of linear carboxylic (fatty) acids are useful progenitors in the formulation of synthetic lubricants and synthetic lubricant additives. Of particular value in these applications are the ester derivatives of said linear carboxylic (fatty) acids with polyols such as pentaerythritol, trimethylol propane and neopentyl glycol.

PROCESS EMBODIMENTS

In the broadest aspect of this invention, unsaturated carboxylic (fatty) acids/esters are prepared from aliphatic conjugated diene substrates by mixing said dienes, in a deoxygenated environment, with a catalytic amount of palladium catalyst precursor, a nitrogen-containing tertiary base, hydroxylated coreactant and carbon monoxide gas and heating said reaction mixture under superatmospheric pressures until the desired unsaturated carboxylic (fatty) acids/esters are formed.

In a narrower practice of this invention, two classes of unsaturated carboxylic (fatty) acids/esters* are prepared concurrently from aliphatic conjugated diene substrates by the catalytic carbonylation and dimerization, carbonylation of said conjugated dienes by a process comprising the following steps:

(a) Admixing each two moles of said aliphatic conjugated diene to be dimerized and/or carbonylated with (1) at least a catalytic quantity of a palladium catalyst precursor consisting of one or more palladium salts in combination with one or more Group VB tertiary donor ligands, and (2) at least a molar equivalent of hydroxylated coreactant selected from the group consisting of water or an aliphatic alkanol containing 1 to 12 carbons, in the presence of an organic nitrogen-containing tertiary base selected from the classes of nitrogen-containing bases which include N-heterocyclic amine bases, aryl-containing tertiary amine bases and aliphatic and aromatic amides.

(b) Pressurizing said reaction mixture with sufficient carbon monoxide to satisfy the stoichiometry of eq. 1 and 2.

(c) Heating said reaction mixture in the temperature range of 30° to 150° C. until substantial formation of desired unsaturated aliphatic carboxylic acids or esters are achieved, and isolating said unsaturated carboxylic (fatty) acids or acid derivatives contained therein.

* The phrase "acids/esters" throughout this application is interchangeable with the phrase "acids or esters."

In order to present the inventive concept in the greatest possible detail as to promote its understanding the following supplementary disclosure is submitted:

A. Process Sequence and Variations

In general, the components of the aforementioned reaction mixture including tertiary nitrogen base, hydroxylated co-reactant, aliphatic conjugated diene and palladium catalyst may be added in any sequence as long as sufficiently good agitation is provided to assure the formation of a homogeneous mixture. For example, the following represent some variations insofar as the catalyst, the sequence of CO added to the reaction mixture and heating that may be made without departing from the inventive process. These modifications include:

(1) The palladium catalyst precursor, consisting of one or more palladium salts in combination with one or more Group VB tertiary donor ligands, may be added to the reaction mixture as separate components. To minimize any stability problems with the homogeneous catalysts, it is preferable to add at least one molar equivalent of Group VB donor ligand, such as bis(1,2-diphenylphosphino)ethane and triphenylphosphine (abbrev. DIPHOS and PPh$_3$ respectively) for each molar equivalent of palladium salt. Optionally, however, a larger excess of Group VB donor ligand may be present before the reaction mixture is heated.

(2) A second variation is that the catalyst is preformed from the palladium salt and Group VB tertiary donor ligands, as described in the literature by Stephenson* and others**, and then added to the reaction mixture as the preformed ligand-stabilized palladium salt, eg. bis(triphenylphosphine) palladium(II) chloride.

*T. A. Stephenson et al., J. Chem. Soc. 3632 (1965).
**A. R. Sanger, J. Chem. Soc. Dalton, 1971 (1977).

(3) A preferred modification of the procedure is that the palladium catalyst, preformed or prepared in situ, is solubilized in a mixture of the hydroxylated coreactant and tertiary nitrogen base prior to the addition of the aliphatic diene, such as 1,3-butadiene, and carbon monoxide.

(4) A substantial process variation that can be employed is to heat the catalyst containing solution to temperature under an inert atmosphere, or a slightly elevated pressure of CO, and then to add the aliphatic diene and carbon monoxide, with efficient agitation, and to maintain the CO pressure in the reactor until the ester is formed.

B. Homogeneous Palladium Catalyst Complex

The homogeneous palladium catalyst complex of this invention normally consists of at least two major components. The first component is a palladium-containing salt. Said palladium may be introduced as the salt of an organic acid, as in the case of palladium(II) acetate, palladium(II) formate, palladium(II) octanoate, palladium(II) propionate, and palladium acetylacetonate. Also suitable, however, are palladium $\pi$-allylic complexes such as Pd($\pi$-allyl)(OAc)$_2$, and palladium salts of mineral acids such as palladium(II) nitrate, palladium sulphate, together with palladium(II) halides such as palladium chloride and palladium bromide.

The second critical component of this homogeneous palladium catalyst is the Group VB tertiary donor ligand. The key elements of these ligands, used to stabilize the palladium(II) salts, are selected from Group VB of the Periodic Chart of the Elements*. They include nitrogen, phosphorus, arsenic and antimony. These elements, in the trivalent oxidation state, particularly tertiary phosphorus, may be bonded to one or more alkyl, cycloalkyl, aryl, substituted aryl, aryloxide, alkyloxide and mixed alkaryl radicals, each containing at least 1 to 12 carbon atoms.
*Advanced Inorganic Chemistry, by F. A. Cotton and G. Wilkinson, 3rd Ed., 1972.

Each donor ligand may contain one, two or more Group VB tertiary donor atoms per molecule and may thereby act as a multidentate ligand* when coordinated to the palladium component of said homogeneous catalyst system.
*Advanced Inorganic Chemistry, by F. A. Cotton and G. Wilkinson, 3rd Ed., 1972.

Illustrative of suitable Group VB tertiary donor ligands, used to stabilize the palladium salts of this invention, are: P(C$_6$H$_5$)$_3$, As(C$_6$H$_5$)$_3$, Sb(C$_6$H$_5$)$_3$, P(CH$_3$)$_2$C$_6$H$_5$, P(iso-C$_4$H$_9$)$_3$, P(CH$_3$)(C$_6$H$_5$)$_2$, P(p-CH$_3$.C$_6$H$_4$)$_3$, P(c-C$_6$H$_{11}$)$_3$, P(OC$_6$H$_5$)$_3$, P(p-CH$_3$.C$_6$H$_4$)(C$_6$H$_5$)$_2$, P(C$_6$H$_5$)$_2$[3,4-(CH$_3$O)$_2$C$_6$H$_3$], P(CH$_3$)$_3$, P(C$_2$H$_5$)$_3$, P(n-C$_4$H$_9$)$_3$, P(C$_8$H$_{17}$)$_3$, P(o-CH$_3$.C$_6$H$_4$)$_3$, (C$_6$H$_5$)$_2$As(CH$_2$)$_2$As(C$_6$H$_5$)$_2$, P(p-Cl.C$_6$H$_4$)$_3$, (C$_6$H$_5$)$_2$P(CH$_3$)P(C$_6$H$_5$)$_2$, (C$_6$H$_5$)$_2$P(CH$_2$)$_2$P(C$_6$H$_5$)$_2$, (C$_6$H$_5$)$_2$P(CH$_2$)$_3$P(C$_6$H$_5$)$_2$*, (C$_6$H$_5$)$_2$PCH=CHP(C$_6$H$_5$)$_2$, PhP(CH$_2$CH$_2$PPh$_2$)$_2$, P(CH$_2$CH$_2$PPh$_2$)$_3$, (C$_6$H$_5$)$_2$AsCH$_2$As(C$_6$H$_5$)$_2$, (C$_6$H$_5$)$_2$As(CH$_2$)$_2$P(C$_6$H$_5$)$_2$**** and (C$_6$H$_5$)$_2$P(CH$_2$)$_4$P(C$_6$H$_5$)$_2$.
**DIPHOS—bis(1,2-diphenylphosphino)ethane, (C$_6$H$_5$)$_2$P(CH$_2$)$_2$P(C$_6$H$_5$)$_2$.
***DIPHOSPr—bis(1,3-diphenylphosphino)propane, (C$_6$H$_5$)$_2$P(CH$_2$)$_3$P(C$_6$H$_5$)$_2$.
****DIARS—bis(1,2-diphenylarsino)ethane, (C$_6$H$_5$)$_2$As(CH$_2$)$_2$As(C$_6$H$_5$)$_2$.

Two preferred classes of homogeneous palladium catalyst complex, particularly useful in the cosynthesis of pentenoate acid esters and nonadienoate acid esters from 1,3-butadiene are:

(a) Palladium halide salts, such as palladium chloride, in combination with monodentate tertiary Group VB donor ligands such as tri-n-butylphosphine, triphenylphosphine, tri-p-tolylphosphine and triethylphosphine, and (b) Palladium halide-free salts, such as palladium acetate, palladium nitrate, palladium acetylacetonate and palladium octanoate, in combination with bidentate and multidentate tertiary Group VB donor ligands such as bis(1,2-diphenylphosphino)ethane, bis(1,3-diphenylphosphino)propane and tris(2-diphenylphosphinoethyl)phosphine.

The following are typical combinations of palladium salt and Group VB tertiary donor ligands which are useful for the catalytic dimerization and/or carbonylation of aliphatic dienes, such as 1,3-butadiene, to their unsaturated carboxylic acid derivatives:
Pd(OAc)$_2$-DIPHOS*, Pd(OAc)$_2$-DIPHOSPr, Pd(OAc)$_2$-DIARS*, Pd(NO$_3$)$_2$-DIPHOS, Pd(ACAC)$_2$-DIPHOS, PdCl$_2$-2P(C$_6$H$_5$)$_3$, PdCl$_2$-2P(CH$_3$)$_2$C$_6$H$_5$, PdCl$_2$-2P(C$_6$H$_{17}$)$_3$, Pd[P(C$_6$H$_5$)$_3$]$_2$Cl$_2$, PdCl$_2$-2P(C$_2$H$_5$)$_3$, PdCl$_2$-2P(p-CH$_3$.C$_6$H$_4$)$_3$ and PdBr$_2$-2P(C$_6$H$_5$)$_3$.
*DIPHOS—bis(1,2-diphenylphosphino)ethane, (C$_6$H$_5$)$_2$P(CH$_2$)$_2$P(C$_6$H$_5$)$_2$
**DIPHOSPr—bis(1,3-diphenylphosphino)propane, (C$_6$H$_5$)$_2$P(CH$_2$)$_3$P(C$_6$H$_5$)$_2$
***DIARS—bis(1,2-diphenylarsino)ethane, (C$_6$H$_5$)$_2$As(CH$_2$)$_2$As(C$_6$H$_5$)$_2$.

The performances of many of these palladium catalyst combinations are illustrated in Tables 1 to 3, infra. Generally, to achieve good yields of desired acid ester products and maximum palladium catalyst stability, at least one molar equivalent of Group VB tertiary donor ligand should be present per gram atom of palladium. Higher ratios are however not deleterious.

C. Ratio of Palladium Catalyst to Aliphatic Diene Substrate

Experimental work indicates that a molar ratio of up to 500 moles of diene per mole of palladium(II) catalyst complex can be employed in most instances where the aliphatic dienes, typified by 1,3-butadiene, are used as the substrate. This molar ratio constitutes what is referred to as a catalytic amount. Much lower ratios (i.e., 25 moles of diene substrate per mole of palladium halide) are not harmful but are economically unattractive. For this reason the preferred molar range is from 50 to 400 moles of diene substrate per mole of palladium metal catalyst.

D. Tertiary Nitrogen Base

The selective production of unsaturated carboxylic (fatty) acids and their derivatives from aliphatic diene substrates is most conveniently carried out in the presence of certain organic tertiary nitrogen bases. Suitable classes of tertiary nitrogen base that are effective in providing improved yields of desired carboxylic acid derivative and improved palladium catalyst stability include heterocyclic nitrogen bases, for example, pyridine, alkylated pyridines such as the picolines, lutidines such as 3,5-lutidine and collidines such as 2,4,6-collidine, pyrazine and alkylated pyrazines such as 2-methylpyrazine, quinoline, isoquinoline and substituted derivatives thereof such as lepidine and guinaldine, and polyaromatic N-heterocyclics, for example, acridine and mixtures thereof.

A second class of suitable tertiary nitrogen base is tertiary aromatic amines, such as N,N-dimethylaniline, N,N-diethylaniline, N,N-diethyltoluidine and N,N-dibutyltoluidine. Additionally, aliphatic and aromatic amides such as N,N-dimethylformamide and N-methyl-2-pyrrolidone and the like are quite effective. All of the above-named nitrogen-containing bases have an ionization constant less than $10^{-8}$*. Stronger tertiary bases, i.e., those having an ionization constant higher than $10^{-8}$, such as triethylamine and N-methylmorpholine, are deleterious and suppress the yield of desired carboxylic acid derivative. Primary and secondary amines such as imidazole, indole, 8-aminoquinoline and tetraethylenepentamine also show lower yields of desired product and, in some cases, evidence for competing octadienyl amine formation.

* "Carbon Monoxide in Organic Synthesis," by J. Falbe, p. 19, 1970.

Confirmation of these preferred classes of tertiary nitrogen bases is illustrated in Tables 1-3, for the syntheses of isopropyl pentenoate and nonadienoate from 1,3-butadiene.

E. Operating Temperature

The temperature range which can be employed for ester formation is variable dependent upon other experimental factors including the substrate employed, the pressure, the concentration and the particular choice of catalyst among other things. Again using butadiene as a typical conjugated aliphatic diene substrate and $PdCl_2-2[P(C_6H_5)_3]$ as a representative catalyst, the range of operability is from about 30° to 150° C. when superatmospheric pressures of CO are employed. A narrower range of 70° C. to 120° C. represents the preferred temperature range when the aforementioned conjugated diene is carbonylated using the catalyst system described supra.

F. Pressure

Superatmospheric pressures of 100 psig to at least 3000 psig lead to substantial conversion of the conjugated diene to the ester of unsaturated carboxylated acid at temperatures of 30° to 150° C. using $PdCl_2-2[P(C_6H_5)_3]$ as catalyst and butadiene as the substrate.

G. Reaction Times Required

As previously indicated in the analogous discussion on temperatures and pressures required in the reaction, experimental variables are important in arriving at reaction times. Generally, substantial conversions (50% or higher) of the conjugated diene substrates to the ester of an unsaturated carboxylic acid can almost always be accomplished within 20 hours with 4 to 18 hours representing the more usual reaction time interval.

H. Conjugated Aliphatic Diene

As used throughout this disclosure, this term refers to a class of conjugated aliphatic linear dienes and cyclic diene substrates wherein the unsaturation in the substrate is only between adjacent carbon-to-carbon atoms. Illustrative of conjugated aliphatic dienes suitable as starting materials in this invention are those having from four to eight carbon atoms per molecule. The preferred aliphatic diene substrate is 1,3-butadiene; other conjugated open-chain diolefins, particularly 1,3-diolefins, that may be useful include 2-methyl-1,3-butadiene (isoprene), 2,3-dimethyl-1,3-butadiene, 2-chloro-1,3-butadiene (chloroprene), 1,3-pentadiene(piperylene), phenyl diolefins and 2,4-hexadiene.

I. Hydroxylated Coreactant

If it is desired to prepare unsaturated carboxylic acids, water must be present in the reaction mixture in sufficient concentration to satisfy the stoichiometry of equations 1 and 2. Where it is desired to prepare unsaturated aliphatic carboxylic acid esters an alcohol coreactant should be included in the reaction mixture with the conjugated aliphatic substrate, palladium catalyst and tertiary nitrogen base. The alcohol may be a monohydric primary, secondary or tertiary alkanol of up to at least twelve carbon atoms, a substituted alcohol, a phenol, or a substituted phenol. Suitable examples include methanol, ethanol, isopropanol, dodecanol, phenol, tert-butanol, 2-chloroethanol, 2-ethylhexanol, methylcyclohexanol and the like. Suitable monohydroxylated coreactants, useful in the synthesis of nonadienoic and pentenoic acid and nonadienoate and pentenoate ester derivatives, are illustrated in Example 22.

Alternatively, the alkanol coreactant may be a polyol containing two or more hydroxyl groupings. Illustrative examples of suitable polyols include propylene glycol, neopentyl glycol, trimethylol propane and pentaerythritol.

J. Carbon Monoxide Environment

Insofar as can be determined, the best selectivities and conversions of the conjugated aliphatic dienes to aliphatic ester can be obtained within a reasonable reaction time by using a substantially carbon monoxide gaseous atmosphere. However, particularly in continuous operation the carbon monoxide may be used in conjunction with from about 0 to 30% by volume of one or more inert gases such as nitrogen, argon, neon and the like without experiencing a substantial decrease in yield and selectivity.

K. Yield

As defined herein, yield is the efficiency in catalyzing the desired diene dimerization and/or carbonylation reaction relative to other undesired reactions. In this instance diene dimerization, carbonylation or diene carbonylation alone are the desired conversions. Yield is expressed as a percentile, and is calculated by determining the amount of desired unsaturated carboxylic acid or acid derivative formed, divided by the amount of conjugated aliphatic diene charged and multiplying the quotient obtained by 100.

L. By-Products

As far as can be determined, without limiting the invention thereby, the one-step dimerization and/or carbonylation of conjugated diene substrates leads primarily to the formation of only one important class of by-products. These by-products, formed only in minor amounts, arise from oligomerization of the conjugated diene to form a higher MW polyene. Where 1,3-butadiene is the substrate, the by-products are principally 4-vinyl-1-cyclohexene and 1,3,7-octatriene.

M. Identification Procedures

Where applicable, the products of this invention are identified by one or more of the following analytical procedures—gas chromatography (GC), infrared (IR) elemental analysis and nuclear magnetic resonance (NMR). Unless otherwise specified, all parts are by weight, all temperatures in degrees centigrade and all pressures in pounds per square inch gauge (psig).

Having described the inventive process in general terms, the following examples are submitted to supply specific and illustrative embodiments.

EXAMPLE 1

THE CO-SYNTHESES OF ISOPROPYL PENTENOATE AND ISOPROPYL NON-ADIENOATE FROM 1,3-BUTADIENE

To a glass-lined autoclave reactor equipped for pressurizing, heating, cooling and means of agitation is added a degassed sample of quinoline (40 ml) and isopropanol (20 ml). Bis(1,2-diphenylphosphino)ethane (0.54 gm) and palladium acetate (0.30 gm) are added under a nitrogen environment and the mixture stirred to give a deep-red solution with some undissolved solids. The reactor is then sealed, deoxygenated with a purge of nitrogen, and butadiene (20 gm, 0.37 mole) injected in from a side ampoule. The reactor is further pressured to 700 psig with carbon monoxide and the mixture heated, with agitation, to 110° C. At the end of 18 hr the reaction is terminated by rapid cooling.

The deep-red liquid product (78 ml) is recovered from the glass liner and analyzed by gas chromatography (GC) as follows:

Yield of isopropyl pentenoate—26 mole %
Yield of isopropyl nonadienoate—13.5 mole %

Elemental analyses of the crude product liquid confirms >90% palladium recovery (basis Pd(OAc)$_2$ charged). The isopropyl nonadienoate and isopropyl pentenoate esters are recovered from the crude liquid mix by fractional distillation, in vacuo. The primary fractions are confirmed by elemental analyses NMR and IR to be the isopropyl 3,8-nonadienoate and isopropyl 3-pentenoate isomers.

EXAMPLE 2

CO-SYNTHESES OF ISOPROPYL PENTENOATE AND ISOPROPYL NON-ADIENOATE FROM 1,3-BUTADIENE

Following the procedure of Example 1, palladium chloride (0.23 gm, 1.3 mmole) and triphenylphosphine (0.70 gm, 2.6 mmole) are added to a degassed sample of isopropanol (20 ml) and isoquinoline (40 ml), the mixture stirred under a nitrogen environment, the reactor sealed and butadiene (20 gm, 0.37 mole) injected in from the side ampoule. After pressurizing to 700 psig with carbon monoxide, the mixture is heated to 110° C., with agitation for 18 hr. At the end of this time the reaction is terminated by rapid cooling.

The deep-red liquid product (81 ml) is recovered from the glass liner and analyzed by gas chromatography (GC) as follows:

Yield if isopropyl pentenoate—26 mole %
Yield of isopropyl nonadienoate—10 mole %

Elemental analyses of the crude liquid product confirms >95% palladium recovery (basis PdCl$_2$ charged) with no visual evidence of palladium precipitation on the liner walls, etc.

The isopropyl nonadienoate and isopropyl pentenoate fractions are recovered from the crude liquid mix by fractional distillation, in vacuo, and identified as primarily isopropyl 3,8-nonadienoate and isopropyl 3-pentenoate respectively.

EXAMPLE 3

CO-SYNTHESES OF ISOPROPYL PENTENOATE AND ISOPROPYL NON-ADIENOATE - MULTIPLE PALLADIUM CATALYST RECYCLE

To a glass-lined autoclave reactor equipped for pressurizing, heating, cooling and means of agitation is added a degassed sample of isoquinoline (40 ml) and isopropanol (20 ml). Bis(1,2-diphenylphosphino)ethane (0.54 gm) and palladium acetate (0.30 gm, 1.34 mmole) are added under a nitrogen environment and the mixture stirred to give a deep-red solution with some undissolved solids. The reactor is sealed, deoxygenated with a purge of nitrogen, and butadiene (20 gm, 0.37 mole) injected in from a side ampoule. The reactor is further pressured to 700 psig with carbon monoxide and the mixture heated, with agitation, to 110° C. At the end of 18 hr the reaction is terminated by rapid cooling. A summary of the GC data for the recovered crude reddish-brown liquid product are given in Table 1.

Table 1

Cosyntheses of Isopropyl Pentenoate and Nonadienoate Esters Multiple Palladium Catalyst Recycle

| Cycle | Catalyst composition | Isopropyl ester yield (mole %) | |
|---|---|---|---|
| | | Non-adienoate | Pentenoate |
| I | Pd(OAc)$_2$-DIPHOS | 13.5 | 19.5 |
| II | Recycle | 28.8 | 15.0 |
| III | Recycle | 38.8 | 10.1 |
| IV | Example 3 residual + DIPHOS | 6.6 | 48.6 |
| V | Recycle | 41.9 | 43.3 |
| VI | " | 42.9 | 11.6 |

Following analyses, the recovered product liquid (78 ml) is recharged to the glass-lined reactor with additional isopropanol (10 ml), a second 20 gm sample of butadiene injected from the side ampoule, and the mixture carbonylated as described supra. Carbonylation of a third butadiene sample (20 gm) is carried out likewise.

After three cycles the crude liquid product (133 ml) is subject to distillation in vacuo. Following removal of the light ends, the fractions distilling at 40°–43° and 56°–58° (1.0–2.0 mm Hg pressure) are substantially isopropyl pentenoate and isopropyl nonadienoate respectively. Further purification of these ester fractions, particularly separation of the isopropyl nonadienoate fraction from remaining isoquinoline solvent may be achieved in a second distillation in vacuo.

Run data for three cycle experiment described above, are summarized in the first portion of Table 1. The data demonstrate Pd(OAc)$_2$-DIPHOS solubilized in isoquinoline, to remain active for pentenoate and nonadienoate ester cosyntheses during multiple cycling. Furthermore, it may be noted that the total C$_5$+C$_9$ acid ester yields actually improve upon successive Pd-catalyst cycling using the palladium halide-free salt and multidentate Group VB tertiary donor ligand combination of this invention.

EXAMPLE 4

CO-SYNTHESES OF ISOPROPYL PENTENOATE AND ISOPROPOYL NON-ADIENOATE FROM 1,3-BUTADIENE - MULTIPLE CYCLING OF RESIDUAL PALLADIUM CATALYST

Following isopropyl pentenoate and nonadienoate ester recoveries by fractional distillation, the residual liquid (13.3 gm) of Example 3 cycle III containing the palladium catalyst is recharged to the glass-lined reactor with bis(1,2-diphenylphosphino)ethane (1.08 gm), isoquinoline (40 ml), isopropanol (20 ml) and butadiene (20 gm) in accordance with the procedure of Example 1. After pressuring to 700 psi with CO, the mixture is heated to 110° C. with agitation, for 18 hr. Termination of the reaction is by rapid cooling. Gas chromatographic data for the deep-red liquid product are summarized in Table 1 (designation, cycle IV).

Following analyses, the recovered product liquid (97 ml) is recharged to the glass-lined reactor with additional isopropanol (10 gm), a further 20 gm of butadiene injected from the side ampoule, and the mixture carbonylated as described supra. Carbonylation of a third butadiene sample is effected similarly, and the crude liquid product (168 ml) fractionally distilled in vacuo to recover desired isopropyl nonadienoate and isopropyl pentenoate fractions (distillate at 56°–58° and 40°–43°, 1–2 mm Hg pressure, respectively).

The residual, deep-red liquid bottoms (21.8 gm) containing the palladium catalyst may be further recycled to the reactor with additional butadiene and isopropanol to generate further quantities of desired $C_5$- and $C_9$-unsaturated acid ester.

It may be noted from the data summarized in the second portion of Table 1, that the palladium catalysts of this invention, solubilized in residual liquid diluent from previous acid ester syntheses (eg. Example 3) remain active for the multiple dimerization/carbonylation of further samples of 1,3-butadiene. Once again total $C_5+C_9$ acid ester yield is maintained during successive cycling of this residual Pd-catalyst.

Table 2

| | Cosyntheses of Isopropyl Pentenoate and Nonadienoate Esters - Multiple Palladium Catalyst Recycle | |
|---|---|---|
| Cycle | Catalyst composition | Isopropyl ester yield (mole %) |
| | | Nonadienoate Pentenoate |
| I | $PdCl_2$-$2PPh_3$ | 10.4   26 |
| II | Recycle | 12.9   22 |
| III | Recycle | 14.9   19 |

EXAMPLE 5

CO-SYNTHESES OF ISOPROPYL PENTENOATE AND ISOPROPYL NONADIENOATE FROM 1,3-BUTADIENE - MULTIPLE PALLADIUM CATALYST RECYCLE

Following the procedure of Example 1, palladium chloride (0.23 gm, 1.30 mmole) and triphenylphosphine (0.70 gm) are added to a degassed sample of isopropanol (20 ml) and isoquinoline (40 ml), the mixture stirred under a nitrogen environment, the reactor sealed and butadiene (20 gm, 0.37 mole) injected in from the side ampoule. After pressuring to 700 psig with carbon monoxide, the mixture is heated to 110° C., with agitation, for 18 hr. At the end of this time the reaction is terminated by rapid cooling. Gas chromatographic analyses of the deep-red crude liquid product are summarized in Table 2.

The recovered product liquid (81 ml) is recharged to the glass-lined reactor, a second 20 gm sample of butadiene injected from the side ampoule, and the mixture carbonylated as described supra. Carbonylation of a third butadiene sample (20 gm) is completed in the presence of additional isopropanol (10 ml), and the crude liquid product (126 ml) subject to vacuum distillation. Isopropyl pentenoate and isopropyl nonadienoate were isolated as liquid distillate fractions.

Again it should be noted (Table 2) that the Pd-catalysts of this invention, in this case $PdCl_2$-$2PPh_3$ solubilized in isoquinoline, show continued good activity upon recycle with fresh 1,3-butadiene charge with no significant loss of palladium due to precipitation, reduction, etc.

Table 3

| | | 1,3-Butadiene Dimerization and/or Carbonylation | | | |
|---|---|---|---|---|---|
| Example | Catalyst composition | Added tertiary amine | Isopropyl ester yield (mole %) | | Pd recovery (%) |
| | | | Nonadienoate | Pentenoate | |
| 6 | $Pd(OAc)_2$-$2PPh_3$ | Lepidine | 58 | <1 | |
| 7 | $Pd(OAc)_2$-$2P(OPh)_3$ | Isoquinoline | 8.0 | <1 | |
| 8 | $Pd(OAc)_2$-$2P(c-C_6H_{11})_3$ | Quinoline | 55 | 1.1 | |
| 9 | $Pd(OAc)_2$-$2P(n-Bu)_3$ | " | 75 | 2.0 | >95 |
| 10 | $Pd(ACAC_2^d$-$2P(n-Bu)_3$ | " | 41 | 3.9 | >95 |
| 11 | $Pd(OAc)_2$-$DIPHOS^a$ | Isoquinoline | 13 | 26 | |
| 12 | $Pd(OAc)_2$-$DIPHOSPr^b$ | Pyridine | 10 | 23 | |
| 13 | $Pd(OAc)_2$-$DIARS^c$ | Quinoline | 0.7 | 0.3 | |
| 14 | $Pd(NO_3)_2$-$DIPHOS^a$ | " | 14 | 28 | |
| 15 | $PdCl_2$-$2P(p-CH_3 . Ph)_3$ | Isoquinoline | 13 | 13 | |
| 16 | $PdCl_22P(CH_3)_2Ph$ | " | 7.1 | 2.9 | >95 |
| 17 | $PdCl_22P(n-Bu)_3$ | Quinoline | 0.1 | 4.3 | >95 |
| 18 | $PdCl_2$-$2PPh_3$ | Isoquinoline | 10 | 26 | >90 |
| 19 | $Pd(PPh_3)_2Cl_2$ | " | 11 | 26 | |
| 20 | $PdCl_2$-DIPHOS | " | 1.2 | 3.2 | |
| 21 | $PdCl_2$-$2PPh_3$ | None | 1.1 | 2.1 | |

$^a$DIPHOS, bis(1,2-diphenylphosphino)ethane
$^b$DIPHOSPr, bis(1,3-diphenylphosphino)propane
$^c$DIARS, bis(1,2-diphenylarsino)ethane
$^d$ACAC, acetylacetone

EXAMPLES 6 TO 21

THE DIMERIZATION/CARBONYLATION OF 1,3-BUTADIENE—EFFECT OF PALLADIUM CATALYST COMPOSITION

In these preparations, the dimerization and carbonylation of 1,3-butadiene to isopropyl nonadienoate and isopropyl pentenoate is carried out in accordance with the procedure of Example 1 using various soluble palladium catalysts, but under constant conditions of temperature, pressure, and initial butadiene-to-Pd ratio. Quinoline and related N-heterocyclic amine bases, predistilled and dried, are the primary solvents in each of these examples. As can be seen from the run data, summarized in Table 3, which follows, a variety of Group VB tertiary donor ligands can be used, in combination with various palladium salts, for the selective synthesis of $C_5$ plus $C_9$ unsaturated acid esters. Suitable Group VB donor ligands, illustrated in Table 3 include monodentate and multidentate tertiary donor ligands containing alkyl, aryl, aryloxide, alkyloxide, cycloalkyl, substituted aryl and mixed alkaryl radicals bonded to tertiary phosphorus and arsenic donor atoms. Illustrated palladium salts include palladium acetate, nitrate, chloride and acetylacetonate together with ligand-stabilized palladium salts such as bis(triphenylphosphine)palladium chloride.

The cosyntheses of pentenoate and nonadienoate esters is best realized with two classes of palladium catalysts, viz:

(a) Palladium halide salts, such as palladium chloride, in combination with monodentate tertiary Group VB donor ligands, such as triphenylphosphine and tri-p-tolylphosphine (Examples 15–19).

(b) Palladium halide-free salts, such as palladium acetate and palladium nitrate, in combination with bidentate or multidentate tertiary Group VB donor ligands such as bis(1,2-diphenylphosphino)ethane and bis(1,3-diphenylphosphino)propane (see Examples 11, 12 and 14).

Both classes of Pd-catalyst may be preformed from the palladium salt and Group VB tertiary donor ligands, as in Example 19, or prepared in situ.

Where said palladium catalyst combinations are solubilized in N-heterocyclic solvents such as quinoline, lipidine, etc., there is generally good Pd recovery in solution, following the butadiene carbonylation step (eg. Examples 9 and 18). In contrast, runs made in the absence of added N-heterocyclic solvent, even with the same catalyst systems (eg. PdCl$_2$-2PPh$_3$) show considerable precipitation of palladium-containing insoluble species and much lower yields of pentenoate and nonadienoate esters (viz., comparative Example 21).

EXAMPLE 22

DIMERIZATION/CARBONYLATION OF 1,3-BUTADIENE—EFFECT OF HYDROXYLATED COREACTANT STRUCTURE

In these examples, using the same experimental procedure as described in Example 1, 1,3-butadiene is dimerized, carbonylated in the presence of typical primary, secondary and tertiary alkanols, including methanol, ethanol, n-propanol, n-butanol, sec-butanol and tert-butanol. Other quantities of reactants, palladium catalyst and heterocyclic amine base remain unchanged. The reaction mixture in each case is sealed and pressured to 700 psig and heated to 110° C. for 6 to 18 hours. The major products are identified in each case as nonadienoate and pentenoate esters, primarily 3,8-nonadienoate and 3-pentenoate esters.

When water is present in excess as the hydroxylated coreactant, then the primary products are pentenoic and nonadienoic acids.

As the numerous examples and preceding discussion have documented, numerous advantages accrue from the practice of this invention both in its compositional and process aspects. For example, a relatively large group of ligand-stabilized palladium catalysts are provided which are useful as catalysts for the one-step dimerization, carbonylation of aliphatic conjugated dienes to their unsaturated carboxylic acid/ester derivatives. Furthermore, it is disclosed that the performances of these catalysts, particularly their activity, stability and selectivity, are significantly improved through the addition of certain tertiary nitrogen bases, defined herein, and that in the presence of said bases, multiple syntheses of desired ester may be readily effected using the same palladium catalyst sample without unacceptable loss of activity or the formation of insoluble palladium species.

Finally, the invention is quite advantageous in that numerous substitutions, modifications and changes can be made without departing from the inventive concept. However, the scope of the subject invention can best be understood by examining the claims which follow, read in conjunction with the preceding specification.

What is claimed is:

1. The process of this invention whereby two classes unsaturated carboxylic (fatty) acids and their ester derivatives are prepared concurrently from aliphatic conjugated diene substrates containing from 4 to 8 carbon atoms according to the procedure of:
    (a) Admixing each two moles of said aliphatic conjugated diene with a three-component mixture consisting of:
        (i) At least a catalytic quantity of a palladium catalyst consisting of either, one or more palladium halide salts in combination with one or more monodentate, tertiary phosphorus-containing donor ligands, or, one or more palladium halide-free salts in combination with one or more multidentate, tertiary phosphorus-containing donor ligands;
        (ii) At least a molar equivalent of hydroxylated coreactant selected from the group consisting of water or an aliphatic alkanol containing 1 to 12 carbon atoms;
        and (iii) An N-heterocyclic amine base, to form a reaction mixture;
    (b) Pressurizing said reaction mixture with sufficient carbon monoxide to satisfy the stoichiometry of the carbonylation reaction;
    (c) Heating said pressurized reaction mixture to temperatures of from 30° to 150° until substantial formation of desired unsaturated aliphatic carboxylic acid derivatives is achieved, and
    (d) Isolating said unsaturated carboxylic (fatty) acid derivatives contained therein.

2. The process of claim 1 wherein the aliphatic conjugated diene substrate is 1,3-butadiene.

3. The process of claim 1 wherein the palladium salt is selected from the group of palladium salts consisting of palladium(II) acetate, palladium(II) nitrate, palladium(II) sulphate, palladium(II) acetylacetonate, palladium(II) chloride and palladium(II) bromide.

4. The process of claim 1 wherein the tertiary phosphorus-containing donor ligands are selected from the group consisting of triphenylphosphine, dimethylphenylphosphine, triethylphosphine, tricyclohexylphosphine, trioctylphosphine, tri-p-tolylphosphine, bis(1,2-diphenylphosphino)ethane, bis(1,3-diphenylphosphino)propane, bis(1,1-diphenylphosphino)methane and tris(2-diphenylphosphinoethyl)phosphine.

5. The process of claim 1 wherein the palladium catalyst is prepared in situ by adding as separate components to the reaction mixture the palladium salts and the tertiary phosphorus-containing donor ligands.

6. The process of claim 1 wherein the palladium catalyst is preformed from the palladium salt and tertiary phosphorus-containing donor ligand components, prior to mixing with conjugated diene substrate, hydroxylated coreactant and nitrogen-containing tertiary base.

7. The process of claim 1 wherein the N-heterocyclic amine base is selected from the group of bases consisting of pyridine, alkylated pyridines, quinoline, isoquinoline, alkylated quinolines and isoquinolines, and acridine.

8. The process of claim 1 for preparing unsaturated carboxylic acid esters wherein said aliphatic alkanol is selected from the group consisting of methanol, ethanol, iso-propanol n-propanol, n-butanol, sec-butanol, and tert-butanol.

9. The process of claim 1 for preparing unsaturated carboxylic acids wherein said hydroxylated coreactant is water.

10. The process of claim 1 for preparing unsaturated carboxylic acid esters wherein said hydroxylated coreactant is a polyol.

11. The process of this invention whereby, following the synthesis of unsaturated carboxylic acids and their derivatives according to the procedure of claim 1, the recovered palladium catalyst, hydroxylated coreactant and N-heterocyclic amine base are reused to convert additional aliphatic conjugated dienes to their unsaturated acid derivatives.

* * * * *